US007245695B2

(12) United States Patent
Mazor et al.

(10) Patent No.: US 7,245,695 B2
(45) Date of Patent: Jul. 17, 2007

(54) DETECTION OF DISHING AND TILTING USING X-RAY FLUORESCENCE

(75) Inventors: Isaac Mazor, Haifa (IL); Alex Dikopoltsev, Haifa (IL); Boris Yokhin, Nazareth Illit (IL); Tzachi Rafaeli, Givat Shimshit (IL); Alex Tokar, Haifa (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 71 days.

(21) Appl. No.: 11/103,071

(22) Filed: Apr. 11, 2005

(65) Prior Publication Data
US 2006/0227931 A1   Oct. 12, 2006

(51) Int. Cl.
*G01N 23/223* (2006.01)
(52) U.S. Cl. ............................. 378/44; 378/50
(58) Field of Classification Search ............ 378/44–50, 378/70–89
See application file for complete search history.

(56) References Cited

U.S. PATENT DOCUMENTS

| | | | | |
|---|---|---|---|---|
| 6,108,398 A | 8/2000 | Mazor et al. | ................. | 378/45 |
| 6,192,103 B1 | 2/2001 | Wormington et al. | .......... | 378/73 |
| 6,389,102 B2 | 5/2002 | Mazor et al. | ................. | 378/89 |
| 6,754,304 B1 | 6/2004 | Kumakhov | ................... | 378/45 |
| 6,810,105 B2 * | 10/2004 | Nasser-Ghodsi et al. | ...... | 378/44 |

OTHER PUBLICATIONS

Singer, "Copper CMP: Taking Aim at Dishing," Semiconductor International (www.reed-electronics.com/semiconductor/), Oct. 2004.
Lankosz article is furnished herewith (previously cited on Sep. 7, 2005) Lankosz et al., "Research in Quantitative X-ray Fluorescence Microanalysis of Patterned Thin Films," Advances In X-Ray Analysis, vol. 43, 1999, pp. 497-503.
Reed Electronics Group, Semiconductor International, "Webcast Equipment Auction" (www.reed-electronics.com/semiconductor/), Dec. 15, 2005.

* cited by examiner

*Primary Examiner*—Edward J. Glick
*Assistant Examiner*—Jurie Yun
(74) *Attorney, Agent, or Firm*—Weingarten, Schurgin, Gagnebin & Lebovici LLP

(57) ABSTRACT

A method for testing a material applied to a surface of a sample includes directing an excitation beam, having a known beam-width and intensity cross-section, onto a region of the sample. An intensity of X-ray fluorescence emitted from the region responsively to the excitation beam is measured. A distribution of the material within the region is estimated, responsively to the measured intensity of the X-ray fluorescence and to the intensity cross-section of the excitation beam, with a spatial resolution that is finer than the beam-width.

25 Claims, 6 Drawing Sheets

DETECTION OF DISHING AND TILTING USING X-RAY FLUORESCENCE

FIELD OF THE INVENTION

The present invention relates generally to non-destructive testing, and particularly to methods and systems for testing of thin film layers formed in the production of semiconductor devices.

BACKGROUND OF THE INVENTION

Manufacturing processes of semiconductor devices are continuously improving in order to support improved technologies and aggressive cost targets. Integrated circuits (ICs) are becoming increasingly complex, integrating higher numbers of components and functions. As semiconductor technology improves, the characteristic component size and layer thickness decreases, allowing more functionality to fit into smaller dies. In parallel, the competitive consumer market drives semiconductor manufacturers to comply with increasingly aggressive cost targets.

The speed and quality of testing semiconductor wafers in the production line has a significant effect on the manufacturing throughput, the achievable yield and the reliability of the finished product. All of these factors affect the final product cost.

One of the methods used for testing semiconductor wafers is X-ray fluorescence (XRF) measurement, and specifically X-ray microfluorescence (i.e., X-ray fluorescence using narrow, focused excitation beams). X-ray fluorescence is a well-known technique for determining the elemental composition of a sample. XRF analyzers generally include an X-ray source, which irradiates the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths of the detected photons, and the qualitative and/or quantitative composition of the sample is determined based on this analysis.

For example, U.S. Pat. No. 6,108,398, whose disclosure is incorporated herein by reference, describes an XRF analyzer and a method for analyzing a sample. The analyzer includes an X-ray beam generator, which generates an X-ray beam incident at a spot on the sample and creates a plurality of fluorescent X-ray photons. An array of semiconductor detectors is arranged around the spot so as to capture the fluorescent X-ray photons. The analyzer produces electrical pulses suitable for analysis of the sample.

The use of X-ray microfluorescence for testing semiconductor wafers is described in U.S. Pat. No. 6,351,516, whose disclosure is incorporated herein by reference. The patent describes a non-destructive method for testing the deposition and/or the removal of a material within a recess on the surface of a sample. An excitation beam is directed onto a region of the sample in a vicinity of the recess, and an intensity of X-ray fluorescence emitted from the region is measured. A quantity of the material that is deposited within the recess is determined responsive to the measured intensity.

Another application of X-ray microfluorescence is described by Lankosz et al., in a paper entitled "Research in Quantitative X-ray Fluorescence Microanalysis of Patterned Thin Films," Advances in X-ray Analysis, volume 43, 1999, pages 497–503, which is incorporated herein by reference. The authors describe a method for X-ray fluorescence microanalysis using a collimated micro-beam. The method is applied for testing the thickness and uniformity of thin films prepared by ion sputtering techniques.

SUMMARY OF THE INVENTION

Currently-available microfluorescence analyzers are limited in their ability to identify features that have a characteristic size smaller than a few tens of microns. As will be shown below, when a microfluorescence analyzer scans a region of a wafer, the resulting XRF profile (i.e., the X-ray fluorescence intensity as a function of position along the scan) may be viewed as a convolution of the layer-thickness profile of the scanned region with the intensity cross-section of the excitation beam. Therefore, the spatial resolution of the XRF profile is limited by the finite beam-width of the X-ray excitation beam. Typically, X-ray beams cannot readily be focused to beam-widths smaller than approximately 20 microns. This limitation is typically due to the performance of the focusing optics and the critical angle defined by the wavelength of the beam.

In many practical applications it is desirable to perform XRF scans with a better resolution, typically on the order of several microns. One such application is the detection of process failures in semiconductor wafer manufacturing processes. Semiconductor wafers contain metallic features, such as contact pads and vias, that have a characteristic size on the order of 50–100 microns. Several known failures that occasionally occur during wafer fabrication are characterized by undesired removal of metal from the surface of a contact pad or a via. These erosion effects, referred to as "dishing" and "tilting," shape the metallic surface of the wafer with a distinctive geometric pattern having a characteristic size of several microns. As will be demonstrated below, conventional XRF analyzers typically do not have sufficient spatial resolution to identify and measure these erosion patterns.

Embodiments of the present invention provide improved methods and systems for performing high-resolution X-ray microfluorescence measurements. These embodiments provide a spatial resolution that is far better than the beam-width of the X-ray excitation beam used, by taking into account the known intensity cross-section function of the beam.

In one embodiment, a contact pad on the surface of a semiconductor wafer is scanned using a conventional microfluorescence analyzer to produce a measured XRF profile of the pad. A simulated pad profile and a model of the excitation beam are convolved to produce a simulated XRF profile. Parameters of the simulated pad profile and beam model are jointly optimized using an iterative optimization process, until the resulting simulated XRF profile fits the measured XRF profile. Following the optimization, a processor extracts quantitative estimates of the dishing and tilting effects in the scanned pad from the optimized simulated pad profile.

The microfluorescence analyzer thus uses the superior spatial resolution provided by the disclosed methods to detect, identify and quantify dishing and tilting effects in semiconductor wafers. The disclosed methods and systems provide the semiconductor manufacturer with valuable information regarding potential failures in the manufacturing process.

There is therefore provided, in accordance with an embodiment of the present invention, a method for testing a material applied to a surface of a sample, including:

directing an excitation beam, having a known beam-width and intensity cross-section, onto a region of the sample;

measuring an intensity of X-ray fluorescence emitted from the region responsively to the excitation beam; and estimating, responsively to the measured intensity of the X-ray fluorescence and to the intensity cross-section of the excitation beam, a distribution of the material within the region with a spatial resolution that is finer than the beam-width.

In a disclosed embodiment, the sample includes a semiconductor wafer, the region includes a metal-filled feature on the wafer, and estimating the distribution includes identifying a defect in the feature. Additionally or alternatively, the defect includes at least one of a dishing effect and a tilting effect.

In another embodiment, directing the excitation beam includes scanning the beam over a feature on the surface, and measuring the intensity includes producing a measured XRF profile of the scanned feature. Additionally or alternatively, measuring the intensity includes subtracting a background noise from the measured XRF profile.

In yet another embodiment, estimating the distribution includes calculating a convolution between a simulated profile of the feature and a beam model representing the intensity cross section of the excitation beam, so as to produce a simulated XRF profile. Additionally or alternatively, the beam model includes at least one Gaussian function.

In still another disclosed embodiment, estimating the distribution includes fitting a simulated XRF profile to the measured XRF profile. Additionally or alternatively, fitting the simulated profile includes applying an iterative optimization process to the simulated XRF profile of the feature. Further additionally or alternatively, applying the iterative process includes calculating a Figure-of-Merit (FOM) function, so as to quantify a difference between the measured XRF profile and the simulated XRF profile. In another embodiment, applying the iterative process includes applying a Genetic Algorithm (GA).

In a disclosed embodiment, the spatial resolution of the estimated distribution is finer than one-half the beam-width.

There is also provided, in accordance with an embodiment of the present invention, apparatus for testing a material applied to a surface of a sample, including:

a radiation source, which is coupled to direct an excitation beam, having a known beam-width and intensity cross-section, onto a region of the sample;

an array of detectors, which are coupled to measure an intensity of X-ray fluorescence emitted from the region responsively to the excitation beam; and a processor, which is arranged to estimate, responsively to the measured intensity of the X-ray fluorescence and to the intensity cross-section of the excitation beam, a distribution of the material within the region with a spatial resolution that is finer than the beam-width.

There is further provided, in accordance with an embodiment of the present invention, a computer software product for testing a material applied to a surface of a sample, the product including a computer-readable medium, in which program instructions are stored, which instructions, when read by the computer, cause the computer to receive an intensity cross-section of an excitation beam, which is used to excite a region of the sample, and to receive a measurement of an intensity of X-ray fluorescence emitted from the region responsively to the excitation beam, and to estimate, responsively to the measurement of the intensity of the X-ray fluorescence and to the intensity cross-section of the excitation beam, a distribution of the material within the region with a spatial resolution that is finer than the beam-width.

The present invention will be more fully understood from the following detailed description of the embodiments thereof, taken together with the drawings in which:

DETAILED DESCRIPTION OF EMBODIMENTS

System Description

Figure 1:
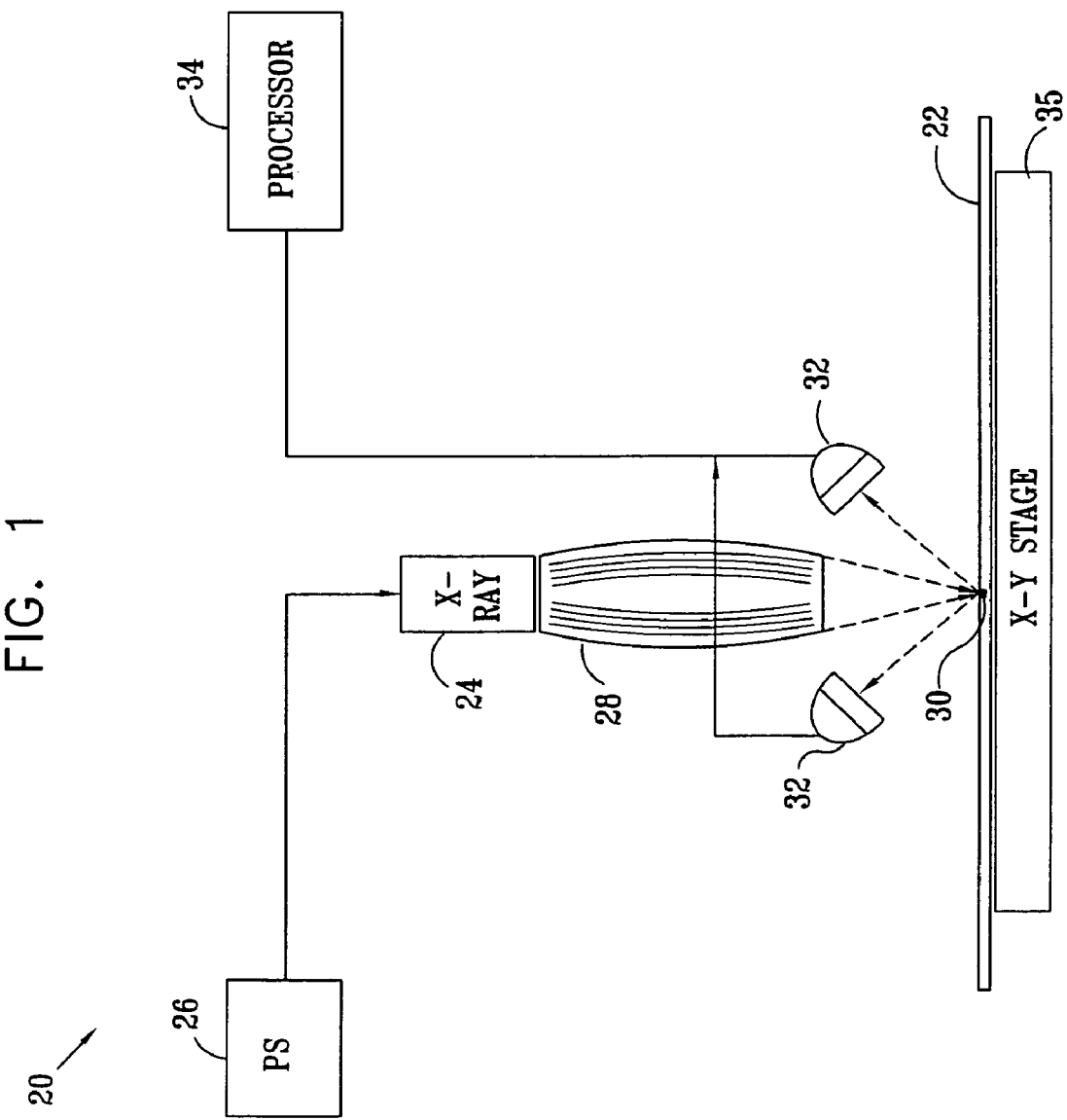
FIG. 1 is a schematic illustration of a system for X-ray microfluorescence measurement, in accordance with an embodiment of the present invention.

FIG. 1 is a schematic illustration of an X-ray microfluorescence analyzer 20, in accordance with an embodiment of the present invention. Aspects of analyzer 20 are described in detail in U.S. Pat. No. 6,108,398 cited above. Analyzer 20 is arranged to examine a sample 22, typically a semiconductor wafer, in order to identify faults in the wafer fabrication process, using methods described hereinbelow.

Analyzer 20 typically comprises an X-ray tube 24, driven by a high-voltage power supply 26, as is known in the art. The X-ray tube emits X-rays having a suitable energy range and power flux into X-ray optics 28. The optics typically comprise a polycapillary array. Optics 28 focus the X-ray beam onto a small region 30, typically a spot on the order of 20 microns in diameter, on the surface of sample 22. The irradiated region emits fluorescent X-rays, which are captured by an array of detectors 32 arranged around region 30 and angled toward it. Detectors 32 generate electrical signals, responsive to the captured photons, which are conveyed to a processor 34.

Alternatively, other types of fluorescence analyzers known in the art, comprising any suitable excitation source, power source, focusing optics and detection system may be used for implementing the methods described herein.

Processor 34 typically comprises an energy-dispersive pulse processing system, as is known in the art, which determines an intensity spectrum of the X-ray photons captured by the detectors. Alternatively, a wavelength-dispersive detection and processing system may be used. Each chemical element within the irradiated region that is excited by the X-rays from tube 24 emits X-rays in characteristic spectral lines. The intensity of the characteristic spectral lines of a given element is proportional to the mass of that element within region 30. Thus, processor 34 uses the determined intensity spectra to determine how much of a particular material is present within the area of region 30.

For purposes of the analysis functions described hereinbelow, processor 34 typically comprises a general-purpose computer processor, which performs these functions under the control of suitable software. This software may be downloaded to the processor 34 in electronic form, over a network, for example, or it may alternatively be provided on tangible media, such as optical, magnetic or non-volatile electronic memory. Further alternatively, the functions described hereinbelow may be implemented in dedicated hardware logic, or using a combination of hardware and software elements.

As shown in FIG. 1, analyzer 20 is used to examine region 30 on sample 22. In one embodiment, the sample is mounted on a movable platform, such as an X-Y stage 35, so as to enable the sample to be moved with respect to the X-ray beam. Alternatively, the sample is mounted on a suitable stationary fixture while tube 24, optics 28 and detectors 32 are moved, so that the X-ray beam scans the sample. Scanning is typically performed over a predetermined coordinate range, following a straight scan line. The result of the scan is a measured XRF profile, indicating the quantity distribution (in other words, the thickness) of the particular material as a function of position along the scan line.

Dishing and Tilting Effects

Figure 2:
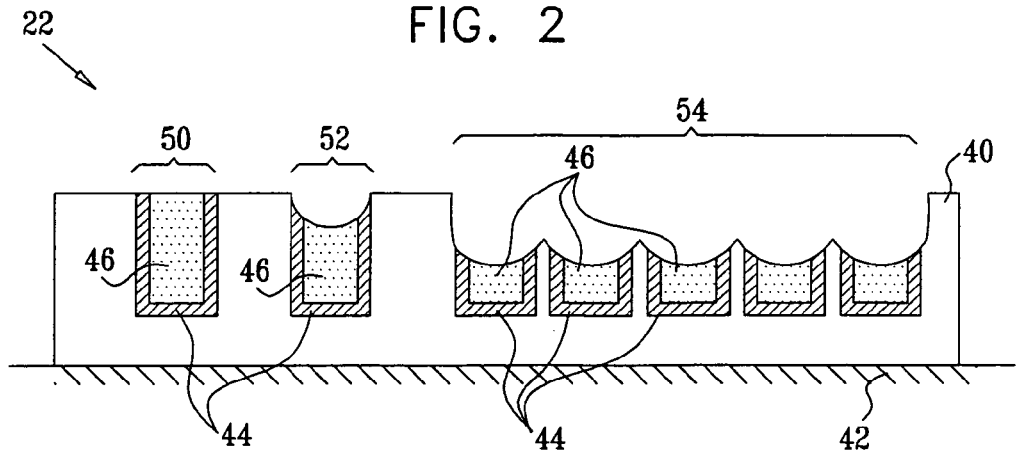
FIG. 2 is a schematic illustration of a sample, showing dishing effects that are detected in accordance with an embodiment of the present invention.

FIG. 2 is a diagram that schematically illustrates part of sample 22, comprising in this example a semiconductor wafer, showing common dishing effects. In a typical wafer fabrication process, the wafer comprises a dielectric layer 40, typically comprising silicon dioxide, formed on a silicon substrate 42. Features such as vias, trenches for conductors and recesses for contact pads are formed in layer 40 by a photolithographic process. These features are to be filled with electrically conducting material, typically copper. In preparation for filling the features with copper, a barrier layer 44 is first deposited onto layer 40, for preventing copper from penetrating into the dielectric layer. The barrier layer typically comprises tantalum. The remaining volume of the features is then filled with a copper filling 46. This process is described here by way of example, as an aid in understanding the operation of some embodiments of the present invention. The principles of the present invention, however, may similarly be applied in detecting dishing effects that occur in materials and processes of other types.

Following the deposition of the different layers, sample 22 undergoes a planarization process, typically comprising a CMP (Chemical-Mechanical Polish) process. In this process, the sample is polished using a polishing pad, which removes the excess copper from the wafer. The polishing process typically uses polishing slurries that contain abrasive particles. The amount of material removed during the CMP process depends upon the pressure exerted by the polishing pad, the abrasive characteristics of the slurry and the different patterns of copper on the surface of the wafer.

A dishing effect may occur during the polishing process when the polishing pad or slurry remove parts of the copper filling from within a via or a contact pad. This excess copper removal creates a characteristic dish-shaped depression, hence the name "dishing." Naturally, dishing is more significant in features that have large copper surfaces. Narrower features such as conductor lines are less susceptible to dishing. Some aspects of the CMP process and a description of dishing and other erosion effects are also described in an article by Singer, entitled "Copper CMP: Taking Aim at Dishing," Semiconductor International (www.reed-electronics.com/semiconductor/), October 2004, which is incorporated herein by reference.

Referring to FIG. 2, the wafer comprises a contact pad 50, which is properly polished. The barrier layer and the copper filling of pad 50 are flush with the surface of dielectric layer 40. A contact pad 52, on the other hand, shows a significant dishing effect. A large portion of the copper filling, as well as some of the barrier layer material, has been undesirably removed by the polishing process. A group 54 of contact pads shows an even more severe effect. In addition to dishing of the individual pads, group 54 also suffers from significant erosion of dielectric layer 40.

Figure 3A:
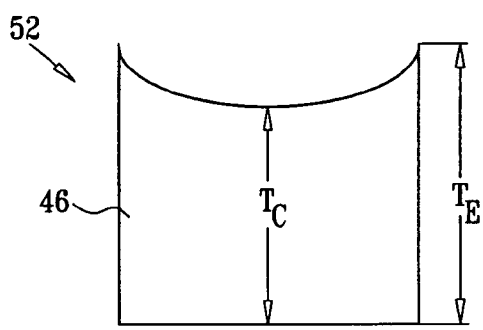
FIG. 3A is a diagram that schematically illustrates a dishing effect that is detected in accordance with an embodiment of the present invention.

FIG. 3A is a diagram that schematically illustrates characteristics of the dishing effect that are measured in accordance with an embodiment of the present invention. The dished shape of the copper filling of pad 52 can be seen in the figure, wherein $T_E$ denotes the copper thickness at the pad edges and $T_C$ denotes the copper thickness at the center of the pad. The dishing of the pad is quantitatively defined as $D=(T_E-T_C)/T_C$. The copper thickness profile is typically modeled as a parabolic function $T(x)=T_c \cdot (1+Dx^2)$, wherein x is the horizontal distance from the center of the pad.

An additional undesired effect of the planarization process is called "tilting," typically resulting from uneven pressure exerted by the polishing pad on a contact pad or a via. The surface of such a via or contact pad is flat, but is tilted diagonally with respect to the surface of dielectric layer 40.

Figure 3B:
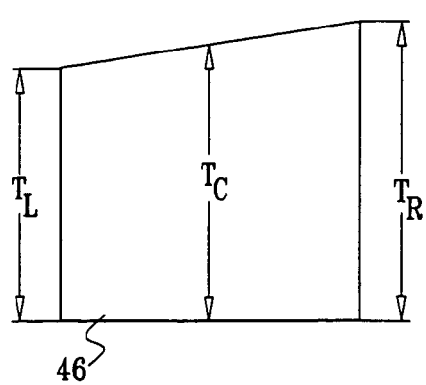
FIG. 3B is a diagram that schematically illustrates a tilting effect that is detected in accordance with an embodiment of the present invention.

FIG. 3B is a diagram that schematically illustrates the tilting effect of a contact pad that is measured in accordance with an embodiment of the present invention. The tilted shape of the copper filling can be seen in the figure, wherein $T_L$, $T_C$, and $T_R$ denote the copper thickness at the left edge, center and right edge of the pad, respectively. The tilting of the pad is quantitatively defined as $Tilt=(T_R-T_L)/T_C$.

In some cases, a contact pad may be both dished and tilted. In such cases, as shown for example by FIG. 4B below, the pad profile is typically modeled as a parabolic shape given by $T(x)=T_c \cdot [1+(Tilt/2) \cdot x+Dx^2]$. In this case the copper has different thicknesses on the left and right edges of the pad.

The geometrical descriptions of FIGS. 3A and 3B above, as well as other geometric illustrations throughout this patent application, illustrate the dishing and tilting effects along one axis only, for the sake of conceptual clarity. In reality, these effects typically erode pads and vias over their entire 2-dimensional surfaces.

Dishing/Tilting Detection Method

As noted above, a major limitation of currently-available microfluorescence measurement methods is their limited spatial resolution. The limited resolution is typically due to the minimum achievable width of the excitation beam, and consequently of the area of irradiated region 30 on the surface of sample 22. A typical diameter for such an irradiated region is on the order of 20 microns, which is of the same order as the characteristic size of a contact pad or a via. Typically, conventional microfluorescence analyzers can only estimate the total mass of copper inside region 30 and indicate whether or not there is a deviation from the expected mass for this region. As the entire mass of copper that is contained within region 30 emits X-ray fluorescence, conventional analyzers cannot resolve details that have characteristic sizes smaller that region 30, such as identifying finer geometrical patterns of the distribution of copper within a contact pad.

An unusually-low mass of copper may be caused by dishing, tilting or other surface erosion mechanisms. The deviation may also be caused by unfilled cavities inside copper filling 46. However, since conventional XRF analyzers cannot resolve the finer details of the copper pattern inside the irradiated region, they cannot identify or characterize the problem.

Embodiments of the present invention provide improved methods for detecting, identifying and quantifying the different erosion mechanisms, by improving the spatial resolution of the microfluorescence analyzer. The disclosed methods are based on the knowledge of the intensity cross-section function of the excitation beam (in other words, the intensity distribution of X-ray flux produced by the beam, as a function of distance from the beam center). Using this information, embodiments of the present invention improve the resolution of measured XRF profiles to well below 10 microns, as will be described below.

Figure 4A:
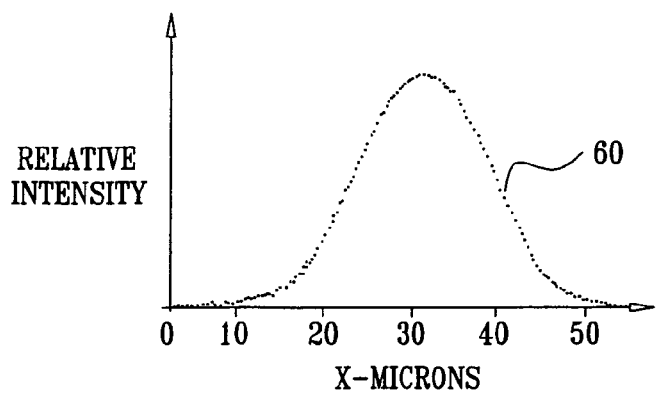
FIG. 4A is a plot that schematically illustrates an intensity cross-section of an X-ray excitation beam, in accordance with an embodiment of the present invention.

FIG. 4A is a plot that schematically illustrates a typical intensity cross-section of an X-ray excitation beam, in accordance with an embodiment of the present invention. A curve 60 shows the relative intensity of the X-ray flux across the beam. The total energy of the beam can be estimated by integrating the area below curve 60. As can be seen in the figure, most of the beam's energy is confined to a width of approximately 20 microns.

Figure 4B:
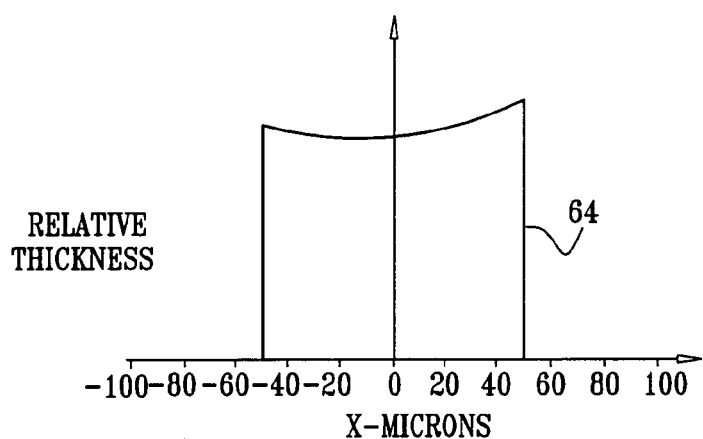
FIG. 4B is a plot that schematically illustrates a copper distribution in a pad that is measured by XRF in accordance with an embodiment of the present invention.

FIG. 4B is a plot that schematically illustrates a copper thickness distribution in a pad, which is measured in accordance with an embodiment of the present invention. A curve 64 shows the relative thickness of copper filling 46 as a function of the horizontal distance from the pad center. The pad described by FIG. 4B has a diameter of approximately 100 microns. The pad suffers from both dishing and tilting, as indicated by the parabolic shape of the profile and the unequal copper thickness at the pad edges.

Figure 4C:
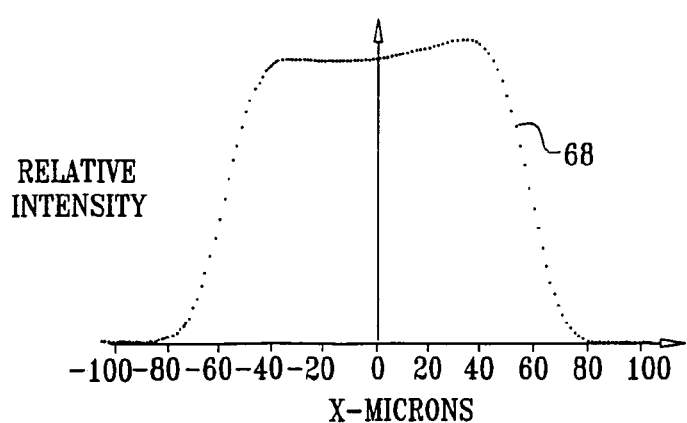
FIG. 4C is a plot that schematically illustrates a measured XRF profile of a pad, in accordance with an embodiment of the present invention.

FIG. 4C is a plot that schematically illustrates a measured XRF profile, in accordance with an embodiment of the present invention. A curve 68 shows the relative intensity of X-ray fluorescence radiation measured by scanning across the pad described by FIG. 4B above with the excitation beam shown in FIG. 4A. Curve 68 shows the fluorescence intensity received by detectors 32 as a function of distance of the center of the X-ray excitation beam from the pad center, while scanning over the pad along the x-axis. Although some deformation of the pad can be observed in curve 68, only coarse features can be seen. The limited resolution of curve 68 is due to the fact that the cross-sectional width of the excitation beam is on the same order of the size of the pad. Curve 68 may be viewed as a convolution of curve 60 (the beam cross section) and curve 64 (the pad profile). The methods described below improve this resolution to a few microns.

Figure 5:
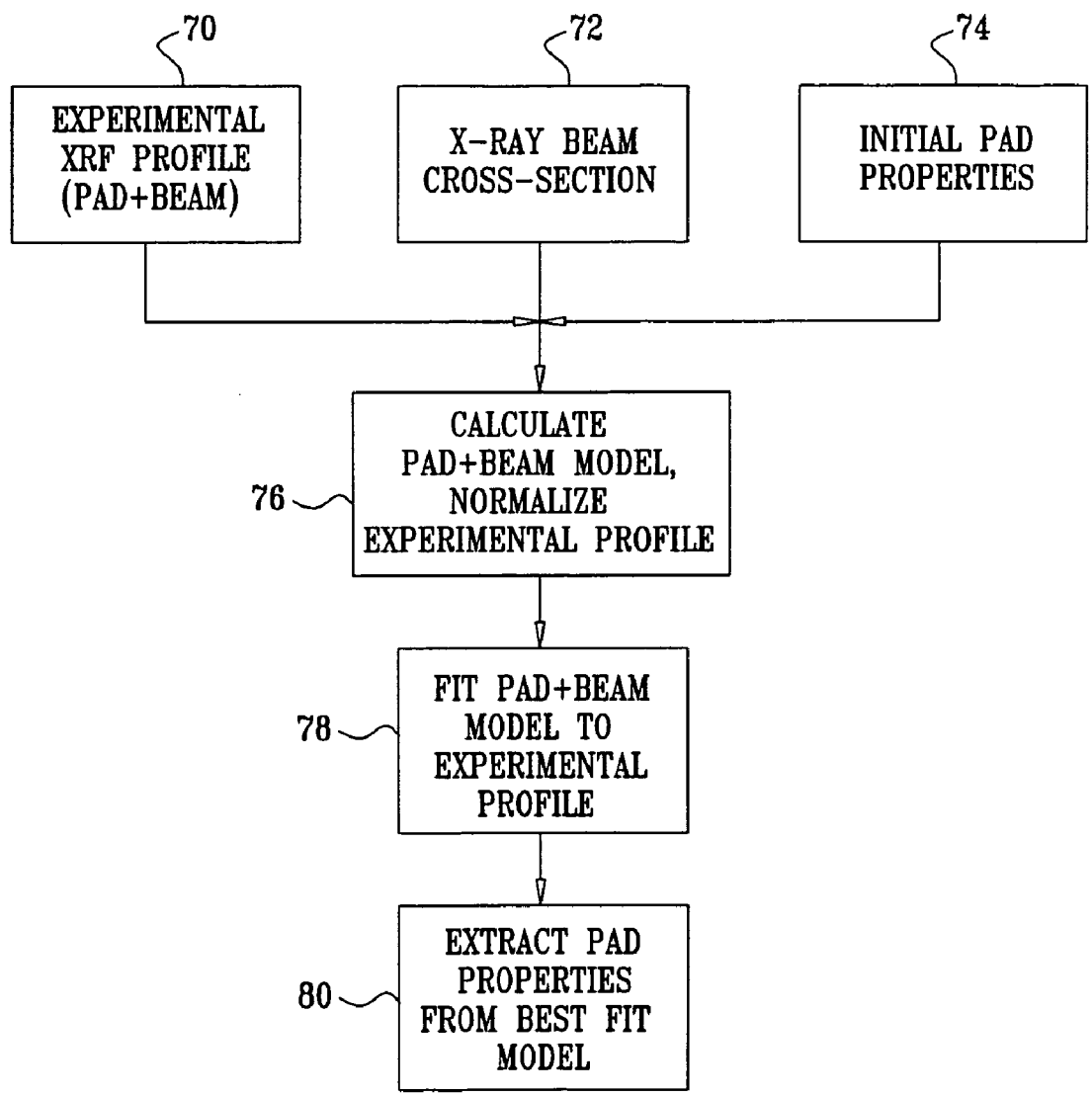
FIG. 5 is a flow chart the schematically illustrates a method for measuring dishing and tilting, in accordance with an embodiment of the present invention.

FIG. 5 is a flow chart that schematically illustrates a method carried out by processor 34 for measuring dishing and tilting, in accordance with an embodiment of the present invention. The method begins with the processor receiving a measured XRF profile, at a profile acceptance step 70. The measured XRF profile is a result of scanning an area of the wafer in system 20 over a predefined scan line, typically covering a tested pad on the surface of the wafer.

Processor 34 also receives an initial model of the intensity cross-section of the X-ray excitation beam (referred to as a "beam model") that is used in acquiring the measured XRF profile, at a beam modeling step 72. Typically, a Gaussian model is used for modeling the beam. In one embodiment, processor 34 uses a default set of parameters defining the beam. Alternatively, a user may specify some or all of the parameters for modeling the Gaussian beam. A typical set of parameters comprises:

- A FWHM (Full Width at Half Maximum) width of the beam.
- Maximum beam intensity.
- Background subtraction parameters such as background offset and slope (in cases in which a linear background model is used. Background subtraction is described in detail in the description of step 76 below.)
- Y-offset, denoting the distance of the scan line from the center of the scanned feature, perpendicular to the axis of the scan line.

In an alternative embodiment, the beam model may be calculated by the processor based on experimental data provided by the user or acquired in system 20 using a suitable high-resolution measurement jig and detector. For example, the user may provide a set of measured data points representing the intensity cross-section. The processor then calculates a beam profile, such as a Gaussian curve, that best fits the measured data points. In another embodiment, the beam model comprises a sum of two Gaussian functions. For example, to compensate for deviation of the tails of the beam profile from the ideal (Gaussian) shape, a first, relatively narrow Gaussian curve may be summed with a second Gaussian curve that has significantly wider FWHM.

The processor constructs a simulated geometrical profile of the pad, at a pad modeling step 74. In one embodiment, the processor uses a default set of parameters for the simulated pad profile. Alternatively, the user can specify some or all of the parameters of the pad profile. A typical set of parameters comprises:

- Pad length—the dimension of the pad parallel to the scan line.
- Pad width—the dimension of the pad perpendicular to the scan line.
- Number of points to be used in the simulated pad profile.
- Dishing—nominal assumed dishing value.
- Tilt—nominal assumed tilting value. (The tilt can be positive or negative, indicating the tilt direction.)
- X-offset—the difference between the nominal and actual center of the pad, in the dimension parallel to the scan line.

The pad profile specified at step 74 and the beam model specified at step 72 above are considered an "initial guess" and are subsequently used as initial conditions to an optimization process, as will be described below. Steps 70, 72 and 74 are mutually independent, and may be performed by processor 34 in any convenient order.

The method continues with processor 34 calculating an initial simulated XRF profile, at a model calculation step 76. As noted above, the XRF profile (whether simulated or measured) is determined by the convolution of the pad profile and the beam intensity cross-section. The processor performs the convolution between the simulated pad profile (obtained at step 74) and the beam model (obtained at step 72), to produce a simulated XRF profile.

Step 76 continues with processor 34 normalizing the measured XRF profile to the simulated XRF profile. In one embodiment, the processor uses a default set of normalization parameters. Alternatively, the user may specify some or all of the parameters. A typical set of normalization parameters comprises:

A multiplicative normalization factor for normalizing the maximum intensity of the measured XRF profile.

A shift parameter for shifting the measured XRF profile in the dimension parallel to the scan line, so as to align the measured and simulated XRF profiles.

An optional background parameter specifying a method of background subtraction. In one embodiment, the processor subtracts the minimum value of the measured XRF profile from all the data points in the profile. Alternatively, the line connecting the left and right edges of the measured XRF profile is calculated. At each x coordinate along the scan line, the value of this line is subtracted from the corresponding data point of the measured XRF profile. Further alternatively, the processor considers a predetermined number of data points at the left and right edges of the measured XRF profile. The processor calculates a line that best fits these points, according to a minimum-square-error criterion. At each x coordinate along the scan line, the value of this line is subtracted from the corresponding data point. Further alternatively, background subtraction parameters may be specified by the user as part of the beam intensity cross-section definition (see step 72 above).

At the conclusion of step 76, processor 34 has generated a simulated XRF profile, based on the beam model and on the simulated pad profile. If the simulated pad profile matches exactly the profile of the actual pad, and if the beam model matches exactly the actual cross-section of the excitation beam, then the simulated XRF profile will match the measured XRF profile received at step 70 above. Any mismatch between the simulated and measured XRF profiles is attributed to differences between the simulated pad profile and the actual pad profile, and between the beam model and the actual beam cross-section. This assumption is the basis for the optimization process that follows.

In order to estimate the parameters of the actual pad, the processor optimizes the parameters of the simulated pad profile and of the beam model by applying an iterative optimization process, at an optimization step 78. Any suitable optimization method may be used for implementing optimization step 78. In each iteration of the optimization process, the processor performs the following steps:

Estimate the difference between the simulated XRF profile and the measured XRF profile, according to a specified Figure-of-Merit (FOM) function. (Several exemplary FOM criteria are described below.)

Based on the estimated difference, modify the parameters of the simulated pad profile and of the beam model, to produce an updated simulated pad profile and beam model.

Calculate a convolution between the updated simulated pad profile and the updated beam model, to produce an updated simulated XRF profile.

The iterative optimization process continues until the difference between the simulated and measured XRF profiles is smaller than a predetermined threshold, according to the FOM function used.

The inventors typically use several alternative FOM functions to estimate the difference between the measured and simulated XRF profiles. For example:

"Statistic" or weighted FOM function, given by $$R = \sqrt{\frac{1}{N} \sum_{i=0}^{N} \frac{1}{Iexp_i} [Iexp_i - Isim_i]^2}$$

wherein $Iexp_i$ denotes the measured (experimental) intensity at data point i, $Isim_i$ denotes the simulated intensity at point i and N denotes the number of points in each of the two XRF profiles.

"SQ" or square-error FOM function, given by $$R = \sqrt{\frac{1}{N} \sum_{i=0}^{N} [Iexp_i - Isim_i]^2}$$

"Normalized SQ" or normalized square-error FOM function, given by $$R = \sqrt{\frac{1}{N} \frac{\sum_{i=0}^{N} [Iexp_i - Isim_i]^2}{maxI_i}}$$

wherein $maxI_i$ denotes the maximum intensity over all points in the measured XRF profile.

In one embodiment, the iterative optimization process described above comprises a Genetic Algorithm (GA, also referred to as an evolutionary algorithm), as is known in the art. Genetic algorithms are often used for fitting a simulated model to experimental data. For example, U.S. Pat. No. 6,192,103, whose disclosure is incorporated herein by reference, describes the use of evolutionary algorithms to find a global solution to the fitting of experimental X-ray scattering data to simulated models.

Returning to the method description, the user typically specifies the following parameters for performing the GA optimization:

A list of parameters to optimize (such as dishing value, tilting value, pad length, x-shift, beam intensity and beam width). For example, the user may optimize only the pad profile parameters and hold the beam model fixed by selecting the appropriate group of parameters.

Nominal initial values for each optimized parameter. These values can also be specified in the initial beam model and pad profile defined in steps 72 and 74, respectively.

Minimum and maximum allowed values for each optimized parameter.

Start and end values, defining the range of calculation of the FOM function.

Maximum number of iterations (generations) of the GA optimization.

Desired FOM criterion.

When the iterative optimization process terminates, the simulated XRF profile comprises the best achievable fit with the measured XRF profile. The updated simulated pad profile comprises a set of parameters that best estimate the parameters of the actual pad.

The processor extracts the estimated pad parameters from the updated simulated pad profile, at a pad estimation step 80. Specifically, the "dishing" parameter in the updated simulated pad profile is an estimate of the dishing value of the actual pad. Similarly, the "tilting" parameter is an estimate of the tilting value of the actual pad. The method terminates with processor 34 outputting the estimated pad parameters.

The estimated pad parameters may be used for identifying the presence and the severity of dishing and tilting effects, so as to assist the semiconductor manufacturer in improving the wafer fabrication process. Typically, the XRF analyzer scans multiple pads and other features in different areas of the wafer, in order to provide useful information regarding process failures.

Although the method described above addressed the measurement of a contact pad, the same method can be applied to any other feature on the surface of the wafer that is susceptible to erosion effects. Additionally or alternatively, the disclosed method may be used to detect and quantify other process failures that are characterized by a change in the geometry or thickness distribution of features in a sample, particularly metal features. Such applications will be apparent to those skilled in the art.

Although system 20 is shown in FIG. 1 in a standalone configuration, elements of this system may alternatively be integrated with semiconductor fabrication equipment whose performance the XRF measurement is meant to monitor. Such integration provides the advantage of on-line or near-on-line detection of process failures. For example, an XRF measurement station may be integrated into a cluster tool.

Dishing/Tilting Detection Example

In order to better explain the dishing/tilting detection method described above, the following example illustrates a typical scenario in which the disclosed method is used to measure dishing and tilting effects in a copper-filled pad. The example uses a Gaussian beam having a FWHM beam-width of 20 microns. The initial pad profile chosen assumes a simple 80×80 micron pad with no dishing or tilting. Fifty data points are used in the simulated pad profile. For the sake of simplicity, no multiplicative normalization and no background subtraction are applied. The only normalization function used is correction of the x-shift between the measured and simulated XRF profiles.

Figure 6A:
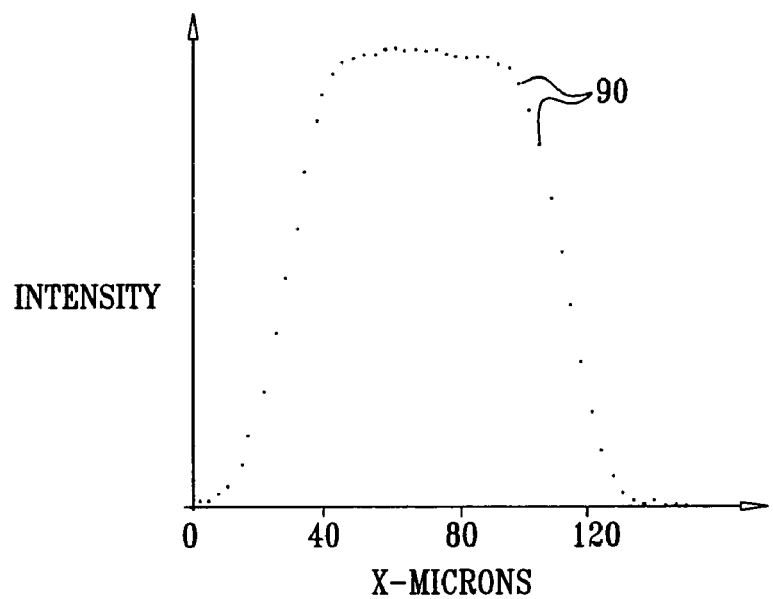
FIG. 6A is a plot that schematically illustrates a measured XRF profile, in accordance with an embodiment of the present invention.

FIG. 6A is a plot that schematically illustrates the measured XRF profile, in accordance with an embodiment of the present invention. A set of data points 90 shows the measured XRF profile, as accepted in step 70 of the method of FIG. 5. Examining data points 90, it is difficult to judge whether or not the scanned pad in the present example suffers from dishing or tilting effects. Data points 90 provide a typical example of the spatial resolution achievable by a conventional XRF analyzer.

Figure 6B:
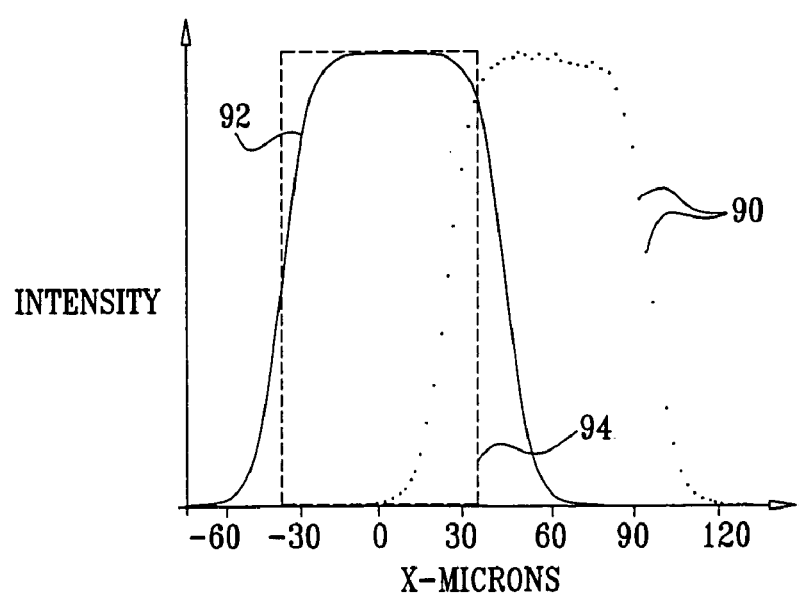
FIG. 6B is a plot that schematically illustrates a simulated XRF profile, in accordance with an embodiment of the present invention.

FIG. 6B is a plot that schematically illustrates the initial simulated XRF profile, in accordance with an embodiment of the present invention. A curve 94 shows the simulated pad profile, as specified in step 74 of the method of FIG. 5. A curve 92 shows the simulated XRF profile, as calculated in step 76. As noted above, the initial simulated pad profile assumes no dishing or tilting, as indicated by the rectangular shape of curve 94.

Figure 6C:
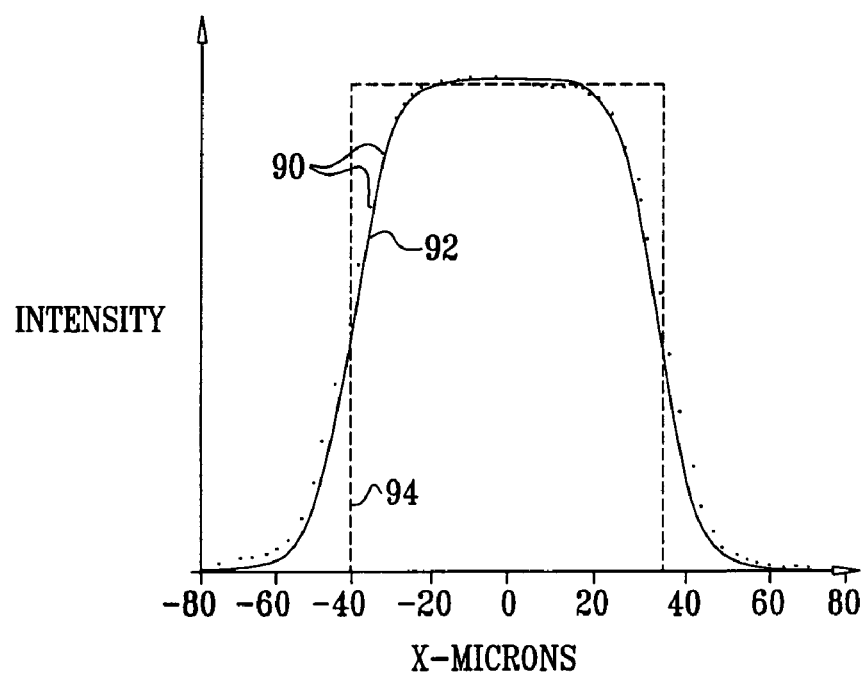
FIG. 6C is a plot that schematically illustrates a normalized XRF profile, in accordance with an embodiment of the present invention.

FIG. 6C is a plot that schematically illustrates a normalized XRF profile, in accordance with an embodiment of the present invention. Data points 90 and curves 92 and 94 show the measured XRF profile, simulated XRF profile and simulated pad profile, respectively, after normalization according to step 76 of the method of FIG. 5. Slight deviations can be seen between data points 90 and curve 92, indicating the differences between the measured and simulated XRF profiles.

Following normalization, an iterative GA optimization process is applied to the simulated profiles, according to step 78 of the method of FIG. 5. The following table lists the parameters to be optimized, the initial conditions and the allowed range for each parameter:

| Parameter | Initial condition | Minimum limit | Maximum limit |
|---|---|---|---|
| Dishing | 0 | −0.1 | 0.1 |
| Tilting | 0 | −0.1 | 0.1 |
| Length (µm) | 80 | 64 | 100 |
| Intensity | 1000 | 800 | 1250 |
| X-shift (µm) | 0 | −1 | 1 |
| Beam width (µm) | 20 | 16 | 25 |

A maximum of 50 generations is allowed. The SQ FOM function described above is used, with start and end values of −140 and 140 microns, respectively. The following table lists the set of best-fit values to which the GA algorithm converged:

| Parameter | Best fit |
|---|---|
| Dishing | 0.039 |
| Tilting | −0.0154 |
| Length (µm) | 82.37 |
| Intensity | 859 |
| X-shift (µm) | −0.09 |
| Beam width (µm) | 22.54 |

Figure 6D:
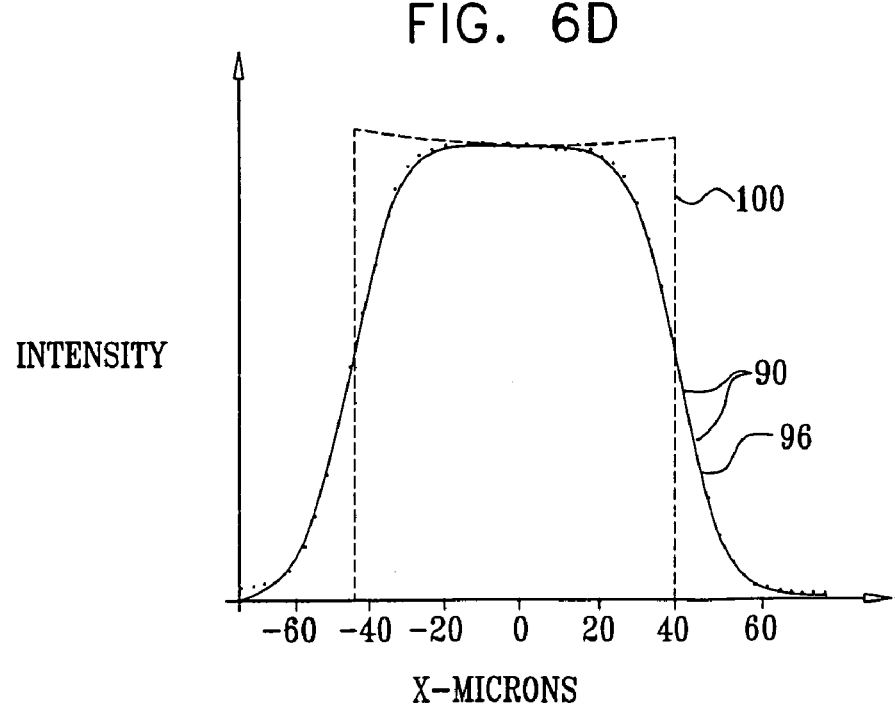
FIG. 6D is a plot that schematically illustrates fitting of a simulated XRF profile to a measured XRF profile, in accordance with an embodiment of the present invention.

FIG. 6D is a plot that schematically illustrates the fitting of the simulated XRF profile to the measured XRF profile, in accordance with an embodiment of the present invention. Data points 90 show the original measured XRF profile. A curve 96 shows the updated simulated XRF profile, following GA optimization according to step 78 of the method of FIG. 5. A curve 100 shows the corresponding updated pad profile. It can be seen that data points 90 and curve 96 are practically congruent, indicating that the GA optimization indeed succeeded in matching the simulated XRF profile to the measured profile.

Curve 100 represents the estimated shape of the pad. As seen in curve 100, the pad suffers from both dishing and tilting. These two effects were unnoticeable in the measured XRF profile illustrated by data points 90. The difference in spatial resolution between data points 90 and curve 100 demonstrates the effectiveness of the disclosed method.

Although the embodiments described hereinabove relate particularly to semiconductor wafer processing, the principles of the present invention may similarly be applied to detect fine details of the distribution of materials on the surface of other types of samples, as well, using X-ray fluorescence. In this context, the term "distribution" refers to any and all local variations in the application of the material. Furthermore, the principles of the present invention may be applied to other techniques of material analysis using X-rays and other forms of ionizing radiation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for testing a material applied to a surface of a sample, comprising:
   directing an excitation beam, having a known beam-width and intensity cross-section, onto a region of the sample;
   measuring an intensity of X-ray fluorescence emitted from the region responsively to the excitation beam;
   estimating, responsively to the measured intensity of the X-ray fluorescence and to the intensity cross-section of the excitation beam, a distribution of the material within the region with a spatial resolution that is finer than the beam-width; and
   outputting an identification of a defect in the region of the sample based on the estimated distribution of the material.

2. The method according to claim 1, wherein the sample comprises a semiconductor wafer, wherein the region comprises a metal-filled feature on the wafer, and wherein estimating the distribution comprises identifying the defect in the feature.

3. The method according to claim 2, wherein the defect comprises at least one of a dishing effect and a tilting effect.

4. The method according to claim 1, wherein directing the excitation beam comprises scanning the beam over a feature on the surface, and wherein measuring the intensity comprises producing a measured XRF profile of the scanned feature.

5. The method according to claim 4, wherein measuring the intensity comprises subtracting a background noise from the measured XRF profile.

6. The method according to claim 4, wherein estimating the distribution comprises calculating a convolution between a simulated profile of the feature and a beam model representing the intensity cross section of the excitation beam, so as to produce a simulated XRF profile.

7. The method according to claim 6, wherein the beam model comprises at least one Gaussian function.

8. The method according to claim 4, wherein estimating the distribution comprises fitting a simulated XRF profile to the measured XRF profile.

9. The method according to claim 8, wherein fitting the simulated profile comprises applying an iterative optimization process to the simulated XRF profile of the feature.

10. The method according to claim 9, wherein applying the iterative process comprises calculating a Figure-of-Merit (FOM) function, so as to quantify a difference between the measured XRF profile and the simulated XRF profile.

11. The method according to claim 9, wherein applying the iterative process comprises applying a Genetic Algorithm (GA).

12. The method according to claim 1, wherein the spatial resolution of the estimated distribution is finer than one-half the beam-width.

13. Apparatus for testing a material applied to a surface of a sample, comprising:
   a radiation source, which is coupled to direct an excitation beam, having a known beam-width and intensity cross-section, onto a region of the sample;
   an array of detectors, which are coupled to measure an intensity of X-ray fluorescence emitted from the region responsively to the excitation beam; and
   a processor, which is configured to estimate, responsively to the measured intensity of the X-ray fluorescence and to the intensity cross-section of the excitation beam, a distribution of the material within the region with a spatial resolution that is finer than the beam-width.

14. The apparatus according to claim 13, wherein the sample comprises a semiconductor wafer, wherein the region comprises a metal-filled feature on the wafer, and wherein the processor is configured to identify a defect in the feature.

15. The apparatus according to claim 14, wherein the defect comprises at least one of a dishing effect and a tilting effect.

16. The apparatus according to claim 13, wherein the radiation source is arranged to scan the beam over a feature on the surface, and wherein the array of detectors is arranged to produce a measured XRF profile of the scanned feature.

17. The apparatus according to claim 16, wherein the processor is configured to subtract a background noise from the measured XRF profile.

18. The apparatus according to claim 16, wherein the processor is configured to calculate a convolution between a simulated profile of the feature and a beam model representing the intensity cross section of the excitation beam, so as to produce a simulated XRF profile of the feature.

19. The apparatus according to claim 18, wherein the beam model comprises at least one Gaussian function.

20. The apparatus according to claim 16, wherein the processor is configured to fit a simulated XRF profile to the measured XRF profile, so as to estimate the distribution of the material.

21. The apparatus according to claim 20, wherein the processor is configured to apply an iterative optimization process to the simulated XRF profile of the feature, so as to fit the simulated XRF profile to the measured XRF profile.

22. The apparatus according to claim 21, wherein the processor is configured to calculate a Figure-of-Merit (FOM) function, so as to quantify a difference between the measured XRF profile and the simulated XRF profile.

23. The apparatus according to claim 21, wherein the iterative optimization process comprises a Genetic Algorithm (GA).

24. The apparatus according to claim 13, wherein the spatial resolution of the estimated distribution is finer than one-half the beam-width.

25. A computer software product for testing a material applied to a surface of a sample, the product comprising a computer-readable medium, in which program instructions are stored, which instructions, when read by the computer, cause the computer to receive an intensity cross-section of an excitation beam, which is used to excite a region of the sample, to receive a measurement of an intensity of X-ray fluorescence emitted from the region responsively to the excitation beam, to estimate, responsively to the measurement of the intensity of the X-ray fluorescence and to the intensity cross-section of the excitation beam, a distribution of the material within the region with a spatial resolution that is finer than the beam-width, and to output an identification of a defect in the region of the sample based on the estimated distribution of the material.

* * * * *